(12) United States Patent
Maier et al.

(10) Patent No.: US 6,339,096 B1
(45) Date of Patent: Jan. 15, 2002

(54) URETHANES DERIVED FROM AZACYCLOALKANES, THE THIO AND DITHIO ANALOGUES THEREOF AND THEIR USE AS CHOLESTEROL BIOSYNTHESIS INHIBITORS

(75) Inventors: Roland Maier; Rudolf Hurnaus; Michael Mark; Bernhard Eisele, all of Biberach (DE); Peter Mueller, Stamford, CT (US); Gebhard Schilcher, Mittelbiberach; Gebhard Adelgoss, Biberach, both of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/275,317

(22) Filed: Mar. 24, 1999

Related U.S. Application Data
(60) Provisional application No. 60/073,027, filed on Jan. 29, 1998.

(51) Int. Cl.⁷ ..................... A61K 31/445; G07D 211/26
(52) U.S. Cl. ................. 514/330; 514/327; 514/331; 546/216; 546/225; 546/229
(58) Field of Search ................. 546/216, 225, 546/229; 514/327, 330, 331

(56) References Cited

U.S. PATENT DOCUMENTS

| | | | |
|---|---|---|---|
| 5,294,625 A | * 3/1994 | Goto et al. | 514/330 |
| 5,962,507 A | * 10/1999 | Woitun | 514/428 |
| 5,998,433 A | * 12/1999 | Takatani | 514/301 |

FOREIGN PATENT DOCUMENTS

| | | | |
|---|---|---|---|
| DE | 44 07 136 | | 9/1995 |
| DE | 44 07 138 | | 9/1995 |
| WO | 99/37643 | * | 7/1999 |

OTHER PUBLICATIONS

Tawada et al. "Preparation of 1–benzoyl–4–naphthalenesulfonyl . . . " CA 130:38404, 1998.*

Bundgaard "Design of prodrugs" Elsevier p.33, 1985.*

Greene "Protective groups in organic synthesis" Wiley & sons, p.218, 220, 224, 251, 1982.*

Chemical Abstracts, vol. 119, No. 5, Aug. 2, 1993; abstract No. 49233t; Goto, G. et al.; "Preparation of 4–benzylpiperidine derivatives for treating edema of brain" (abstract of JP 04 312572).

Chang, George; Ruggeri, Roger B.; "Recent developments in the treatment of dyslipidaemia"; Expert Opinion On Therapeutic Patents; May 1997; pp. 441–455; Bd. 7, Nr. 5; Ashley Publications, Ltd.; US.

* cited by examiner

*Primary Examiner*—Ceila Chang
(74) *Attorney, Agent, or Firm*—Robert P. Raymond; Timothy X. Witkowski; Alan R. Stempel

(57) ABSTRACT

The present invention relates to urethanes derived from azacycloalkanes and the thio and dithio analogues thereof of general formula (I)

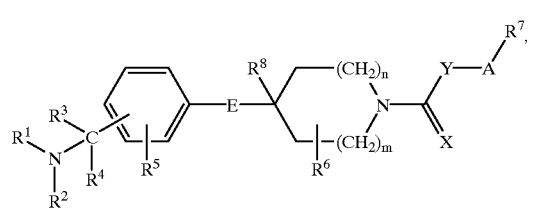

wherein m, n, A, X, Y, E and $R^1$ to $R^8$ are defined as in claim 1, the enantiomers, diastereomers and the salts thereof, particularly the physiologically acceptable acid addition salts thereof which have valuable properties, particularly an inhibitory effect on cholesterol biosynthesis, pharmaceutical compositions containing these compounds, their use and processes for preparing them.

8 Claims, No Drawings

URETHANES DERIVED FROM AZACYCLOALKANES, THE THIO AND DITHIO ANALOGUES THEREOF AND THEIR USE AS CHOLESTEROL BIOSYNTHESIS INHIBITORS

This application claim benefit to provisional No. 60/073,027 filed Jan. 21, 1998.

The present invention relates to new urethanes derived from azacycloalkanes, the thio and dithio analogues thereof, the salts thereof with physiologically acceptable organic and inorganic acids, processes for preparing these compounds and pharmaceutical compositions containing them.

The compounds according to the invention are inhibitors of cholesterol biosynthesis, particularly inhibitors of the enzyme 2,3-epoxysqualene-lanosterol-cyclase, a key enzyme in cholesterol biosynthesis. The compounds according to the invention are suitable for the treatment and prophylaxis of hyperlipidaemias, hypercholesterolaemias and atherosclerosis. Other possible applications are in the treatment of hyperproliferative skin and vascular diseases, tumours, gallstone problems and mycoses.

Compounds which affect cholesterol biosynthesis are important for the treatment of a number of diseases. These include in particular hypercholesterolaemias and hyperlipidaemias which are risk factors for the occurrence of atherosclerotic vascular changes and their sequelae such as coronary heart disease, cerebral ischaemia, Claudicatio intermittens and gangrene.

The significance of elevated serum-cholesterol levels as a main risk factor for the occurrence of atherosclerotic vascular changes is generally known. Extensive clinical studies have led to the finding that the risk of developing coronary heart diseases can be reduced by lowering serum cholesterol (Current Opinion in Lipidology 2(4), 234 [1991]; Exp. Opin. Ther. Patents 7(5), 441–455 [1997]). Since the majority of the cholesterol is synthesised in the body itself and only a small proportion is taken in with the food, inhibiting biosynthesis is a particularly attractive method of lowering raised cholesterol levels.

In addition, other possible applications for cholesterol biosynthesis inhibitors are the treatment of hyperproliferative skin and vascular diseases and tumours, the treatment and prophylaxis of gallstone problems and their use in treating mycoses. The latter case involves intervening in the ergosterol biosynthesis in fungal organisms which proceeds substantially analogously to cholesterol biosynthesis in mammalian cells.

The cholesterol or ergosterol biosynthesis takes place, starting from acetic acid, via a large number of reaction steps. This multi-stage process offers a number of possible interventions, of which the following are examples:

For inhibiting the enzyme 3-hydroxy-3-methylglutaryl-coenzyme A (HMG-CoA)-synthase, β-lactones and β-lactams with a potential antihypercholesterolaemic activity are mentioned (cf. J. Antibiotics 40, 1356 [1987], U.S. Pat. No. 4,751,237, EP-A-0 462 667, U.S. Pat. No. 4,983,597).

Examples of inhibitors of the enzyme HMG-CoA-reductase are 3,5-dihydroxycarboxylic acids of the mevinolin type and their δ-lactones, of which lovastatin, simvastatin, pravastatin, fluvastatin, atorvastatin and cerivastatin are used in the treatment of hypercholesterolaemias. Other possible applications for these compounds are fungal infections (U.S. Pat. No. 4,375,475, EP-A-0 113 881, U.S. Pat. No. 5,106,992), skin diseases (EP-A-0 369 263) and gallstone problems and tumour diseases (U.S. Pat. No. 5,106,992; Lancet 339, 1154–1156 [1992]).

The inhibition of the proliferation of smooth muscle cells by lovastatin is described in Cardiovasc. Drugs. Ther. 5, Suppl. 3, 354 [1991]. Tocotrienol, an unsaturated analogue of vitamin E, and its analogues make up another class of substances which act on HMG-CoA-reductase (Exp. Opin. Ther. Patents 7 (5), 446 [1997]). Inhibitors of the enzyme squalene-synthetase are e.g. isoprenoid-(phosphinylmethyl)-phosphonates, the suitability of which for treating hypercholesterolaemias, gallstone problems and tumour diseases is described in EP-A-0 409 181 and in J. Med. Chemistry 34, 1912 [1991], and also α-phosphonosulfinate compounds (EP-A-0 698 609), the compounds J-104,118 and J-104,123 (Tetrahedron 52, 13881–13894, [1996]) and cyclobutane derivatives (WO 96/33159). A survey of squalene-synthethase inhibitors can be found in Exp. Opin. Ther. Patents 7 (5), 446–448 [1997].

Known inhibitors of the enzyme squalene-epoxidase are allylamines such as naftifine and terbinafine, which have been used in therapy to fight fungal diseases, and also the allylamine NB-598 with an antihypercholesterolaemic activity (J. Biol. Chemistry 265, 18075–18078 [1990]) and fluorosqualene derivatives with a hypocholesterolaemic activity (U.S. Pat. No. 5,011,859). Moreover, piperidines and azadecalines with a potential hypocholesterolaemic and/or antifungal activity are described, the mechanism of activity of which has not been fully explained and which are squalene epoxidase and/or 2,3-epoxisqualene-lanosterol-cyclase inhibitors (EP-A-0 420 116, EP-A-0 468 434, U.S. Pat. No. 5,084,461 and EP-A-0 468 457). Other examples are described in Exp. Opin. Ther. Patents 7 (5), 448–449 [1997].

Examples of inhibitors of the enzyme 2,3-epoxisqualene-lanosterol-cyclase are diphenyl derivatives (EP-A-0 464 465), aminoalkoxybenzene derivatives (EP-A-0 410 359, J. Lipid. Res. 38, 373–390, [1997]) and piperidine derivatives (J. Org. Chem. 57, 2794–2903 [1992] which have an antifungal activity. Moreover this enzyme is inhibited in mammalian cells by decalines, azadecalines and indane derivatives (WO 89/08450; J. Biol. Chemistry 254, 11258–11263 [1981]; Biochem. Pharmacology 37, 1955–1964 [1988] and J 64 003 144), and also by 2-aza-2,3-dihydro-squalene and 2,3-epiminosqualene (Biochem. Pharmacology 34, 2765–2777 [1985]), by squalenoid-epoxide-vinylether (J. Chem. Soc. Perkin Trans. I, 461 [1988]) and 29-methylidene-2,3-oxidosqualene (J. Amer. Chem. Soc. 113, 9673–9674 [1991]). Other examples are pyridine and pyrimidine derivatives (WO 97/06802), heterobicyclic alkylamines (WO 96/11201), imidazole derivatives (EP-A-0 757 988) and isoquinoline derivatives (J. Med. Chemistry 39, 2302–2312, [1996]). Other compounds described are ureas (DE-A-4 438 021), oximes (DE-A-4 412 692), a number of amides (DE-A-4 407 134, DE-A-4 407 135, DE-A-4 407 136, DE-A-4 407 138, DE-A-4 407 139, DE-A-4 412 691, DE-A-4 437 999, DE-A-4 438 000, DE-A-4 438 020, DE-A-4 438 082, DE-A-4 438 029, DE-A-4 438 054, DE-A-4 438 055, DE-A-4 438 082, DE-A-4 438 083, EP-A-0 599 203, EP-A-0 596 326) and esters (WO 95/29148). Other examples are described in Exp. Opin. Ther. Patents 7(5), 448–449 [1997].

Finally, inhibitors of the enzyme lanosterol-14α-demethylase also include steroid derivatives with a potential antihyperlipidaemic activity which simultaneously influence the enzyme HMG-CoA-reductase (U.S. Pat. No. 5,041,431; J.Biol. Chemistry 266, 20070–20078 [1991]; U.S. Pat. No. 5,034,548). This enzyme is also inhibited by the antimycotics of the azole type which constitute N-substituted imidazoles and triazoles. This class includes, for example, the commercially available antimycotics ketoconazole and fluconazole.

The compounds of the following general formula I are new. It has been found that, surprisingly, they are highly effective inhibitors of the enzyme 2,3-epoxisqualene-lanosterol-cyclase (International Classification: EC 5.4.99.7).

The enzyme 2,3-epoxisqualene-lanosterol-cyclase catalyses a key step of cholesterol or ergosterol biosynthesis, namely the conversion of 2,3-epoxisqualene into lanosterol, the first compound with a steroid structure in the biosynthesis cascade. Inhibitors of this enzyme lead one to expect the advantage of higher selectivity, compared with inhibitors of earlier stages of biosynthesis, such as for example HMG-CoA-synthase and HMG-CoA-reductase, CoA-reductase since inhibiting these early stages of biosynthesis leads to a reduction in biosynthetically formed mevalonic acid and consequently may have a negative effect on the biosynthesis of the mevalonic acid-dependent substances dolichol, ubiquinone and isopentenyl-t-RNA (cf. J. Biol. Chemistry 265, 18075–18078 [1990]).

When stages of biosynthesis after the conversion of 2,3-epoxysqualene into lanosterol are inhibited, there is a risk of the accumulation of intermediate products with a steroid structure in the body and the triggering of toxic effects caused by them. This has been described, for example, in the case of triparanol, a desmosterol-reductase inhibitor. This substance had to be taken off the market on account of the formation of cataracts, ichthyosis and alopecia (mentioned in J. Biol. Chemistry 265, 18075–18078 [1990]).

As already stated hereinbefore, inhibitors of 2,3-epoxisqualene-lanosterol-cyclase have already been described in the literature. However, absolutely no urethanes or their thio or dithio analogues are known as inhibitors of 2,3-epoxisqualene-lanosterol-cyclase.

The invention relates to the preparation of antihypercholesterolaemic substances which are suitable for the treatment and prophylaxis of atherosclerosis and are distinguished from known active substances by their superior antihypercholesterolaemic activity with greater selectivity and hence greater safety. Since the compounds according to the invention are also able to inhibit ergosterol biosynthesis in fungal organisms by virtue of their great efficacy as inhibitors of the enzyme 2,3-epoxisqualene-lanosterol-cyclase, they are also suitable for treating mycoses.

The present invention relates to the new urethanes derived from azacycloalkanes and the thio and dithio analogues thereof of general formula

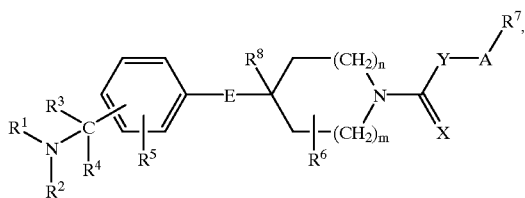

(I)

wherein
m denotes the numbers 0 or 1,
n denotes the numbers 1 or 2,
A denotes a single bond, a straight-chained or branched $C_{1-8}$-alkylene group, a $C_{2-8}$-alkenylene or $C_{2-8}$-alkynylene group, whilst an unsaturated group is not directly bound to the group y, X denotes an oxygen or sulphur atom,
Y denotes an oxygen or sulphur atom,
$R^1$ denotes a straight-chained or branched $C_{1-6}$-alkyl group, a $C_{1-4}$-alkenyl group or a $C_{1-4}$-alkynyl group, whilst the multiple bond is isolated from the nitrogen-carbon bond,
$R^2$ denotes a straight-chained or branched $C_{1-6}$-alkyl group, a $C_{1-4}$-alkenyl group or a $C_{1-4}$-alkynyl group, whilst the multiple bond is isolated from the nitrogen-carbon bond, or
$R^1$ and $R^2$ together with the nitrogen atom denotes a 5- to 7-membered, saturated heterocyclic ring wherein a methylene group isolated from the nitrogen atom may be replaced by an oxygen or sulphur atom or by an —NH— or —N(alkyl)-group,
$R^3$ to $R^6$, which may be identical or different, denote hydrogen atoms or alkyl groups,
$R^7$ denotes a $C_{3-7}$-cycloalkyl group, a phenyl or naphthyl group optionally substituted by one or two halogen atoms or by an alkyl, alkoxy, trifluoromethyl or cyano group or, if A does not denote a single bond, $R^7$ also denotes a hydrogen atom,
E denotes an oxygen or sulphur atom, a methylene, carbonyl or sulphinyl group and
$R^8$ denotes a hydrogen atom or
E denotes the group —C($R^9R^{10}$)—, wherein
$R^9$ denotes a hydrogen atom and
$R^{10}$ together with the adjacent group $R^8$ denotes a carbon-carbon bond,
whilst, unless otherwise stated, alkyl groups contained in the groups mentioned above may contain 1 to 3 carbon atoms and a halogen atom mentioned above may be a fluorine, chlorine or bromine atom,
the enantiomers, diastereomers, the mixtures thereof and the salts thereof, particularly the physiologically acceptable acid addition salts thereof. The preferred compounds are the compounds of general formula I, wherein
m denotes the number 1,
n denotes the number 1,
A denotes a single bond, a straight-chained or branched $C_{1-4}$-alkylene group or a $C_{2-4}$-alkenylene group, wherein an unsaturated group is not directly bound to the group Y,
X denotes an oxygen or sulphur atom,
Y denotes an oxygen or sulphur atom,
$R^1$ denotes a straight-chained or branched $C_{1-6}$-alkyl group, an allyl or propargyl group, whilst the multiple bond is isolated from the nitrogen-carbon bond,
$R^2$ denotes a straight-chained or branched $C_{1-6}$-alkyl group, an allyl or propargyl group, whilst the multiple bond is isolated from the nitrogen-carbon bond,
$R^1$ and $R^2$ together with the nitrogen atom denote a 5- to 7-membered, saturated heterocyclic ring wherein a methylene group isolated from the nitrogen atom may be replaced by an oxygen or sulphur atom,
$R^3$ to $R^6$, which may be identical or different, denote hydrogen atoms or methyl groups,
$R^7$ denotes a $C_{3-6}$-cycloalkyl group, a phenyl or naphthyl group optionally substituted by one or two halogen atoms or by an alkyl, alkoxy, trifluoromethyl or cyano group,
E denotes a sulphur atom, a methylene, carbonyl or sulphinyl group and $R^8$ denotes a hydrogen atom or E denotes the group $—C(R^9R^{10})—$ whilst
$R^9$ denotes a hydrogen atom and
$R^{10}$ together with the adjacent group $R^8$ denotes a carbon-carbon bond, whilst, unless otherwise stated, alkyl groups contained in the groups mentioned above may each contain 1 to 3 carbon atoms and a halogen atom mentioned above may be a fluorine, chlorine or bromine atom, the enantiomers, diastereomers, the mixtures thereof and the salts thereof, particularly the physiologically acceptable acid addition salts thereof.

Particularly preferred are the compounds of general formula I, wherein m denotes the number 1, n denotes the number 1, A denotes a single bond or a straight-chained or branched $C_{1-3}$ alkylene group, X denotes an oxygen or sulphur atom, Y denotes an oxygen or sulphur atom, $R^1$ denotes a straight-chained or branched $C_{1-3}$-alkyl group, $R^2$ denotes a straight-chained or branched $C_{1-3}$-alkyl group, or $R^1$ and $R^2$ together with the nitrogen atom denote a piperidino or morpholino group, $R^3$ to $R^6$ denote hydrogen atoms, $R^7$ denotes a cyclohexyl group or a phenyl group optionally substituted by a halogen atom or by an alkyl, alkoxy or trifluoromethyl group, E denotes a sulphur atom, a methylene group, a carbonyl or sulphinyl group and $R^8$ denotes a hydrogen atom or E denotes the group $—C(R^9R^{10})—$, wherein
$R^9$ denotes a hydrogen atom and
$R^{10}$ together with the adjacent group $R^8$ denotes a carbon-carbon bond, the enantiomers, diastereomers, the mixtures thereof and the salts thereof, particularly the physiologically acceptable acid addition salts thereof.

Most particularly preferred are the compounds of general formula I wherein m denotes the number 1, n denotes the number 1, A denotes a single bond or a methylene group, X denotes an oxygen or sulphur atom, Y denotes an oxygen or sulphur atom, $R^1$ and $R^2$ each denote a methyl group, $R^3$ to $R^6$ denote hydrogen atoms, $R^7$ denotes a phenyl group optionally substituted by a fluorine or chlorine atom or by a methyl group, E denotes a sulphur atom, a methylene or carbonyl group and $R^8$ denotes a hydrogen atom or E denotes the group $—C(R^9R^{10})—$, wherein
$R^9$ denotes a hydrogen atom and
$R^{10}$ together with the adjacent group $R^8$ denotes a carbon-carbon bond, the mixtures and salts thereof, particularly the physiologically acceptable acid addition salts thereof, but particularly the compounds (1) N-(benzylthio)thiocarbonyl-4-[4-(dimethylaminomethyl)phenylthio]piperidine, (2) N-(benzylthio)thiocarbonyl-4-[4-(dimethylaminomethyl)benzoyl]piperidine, (3) N-benzyloxycarbonyl-4-[4-(dimethylaminomethyl)phenylthio]piperidine, (4) N-(4-chlorophenoxy)carbonyl-4-[4-(dimethylaminomethyl)phenylthio]piperidine, (5) N-(benzylthio)thiocarbonyl-4-[4-(dimethylaminomethyl)benzyl]piperidine, (6) N-(benzylthio)thiocarbonyl-4-[4-(dimethylaminomethyl)benzylidene]piperidine, (7) N-(4-chlorophenoxy)thiocarbonyl-4-[4-(dimethylaminomethyl)benzyl]piperidine, (8) N-(4-chlorophenoxy)carbonyl-4-[4-(dimethylaminomethyl)benzyl]piperidine, (9) N-benzyloxycarbonyl-4-[4-(dimethylaminomethyl)benzyl]piperidine,

(10) 4-[4-(dimethylaminomethyl)benzyl]-N-(4-methylphenoxy)carbonylpiperidine,

(11) 4-[4-(dimethylaminomethyl)benzyl]-N-(4-methylphenoxy)thiocarbonylpiperidine and

(12) 4-[4-(dimethylaminomethyl)benzyl]-N-(4-fluorphenoxy)carbonylpiperidine, the mixtures and the salts thereof, particularly the physiologically acceptable acid addition salts thereof, such as the hydrochlorides, methanesulphonates or tartrates thereof.

The compounds of general formula I may be prepared for example by the following methods:

a) reacting a compound of general formula

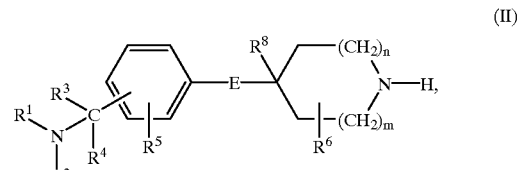

(II)

wherein
m, n, E with the exception of the sulphinyl group, $R^1$ to $R^6$ and $R^8$ are as hereinbefore defined, with a compound of general formula

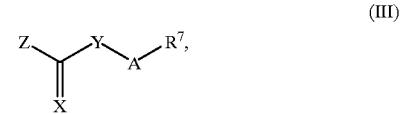

(III)

wherein
A, X, Y and $R^7$ are as hereinbefore defined and Z denotes a leaving group, e.g. a halogen atom such as a chlorine, bromine or iodine atom.

The reaction is carried out under Schotten-Baumann or Einhorn conditions, i.e. the components are reacted in the presence of at least one equivalent of an auxiliary base at temperatures of between −50° C. and +120° C., preferably −10° C. and +30° C., and optionally in the presence of solvents. Preferred auxiliary bases are alkali and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, and tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, whilst preferred solvents include, for example, diethylether, methylene chloride, dichloromethane, ethyl acetate, toluene, tetrahydrofuran, 1,4-dioxane, acetonitrile, dimethylformamide, dimethylacetamide, N-methylpyrrolidone or mixtures thereof; if alkali or alkaline earth metal hydroxides, alkali metal carbonates or acetates are used as auxiliary bases, water may also be added to the reaction mixture as a cosolvent.

b) In order to prepare compounds of general formula (I), wherein X and Y each denote a sulphur atom and m, n, A, E and $R^1$ to $R^8$ are as hereinbefore defined with the proviso that $R^7$ does not represent an optionally substituted phenyl or naphthyl group if A denotes a single bond:

reacting compounds of general formula (II), wherein m, n and E with the exception of the sulphinyl group, $R^1$ to $R^6$ and $R^8$ are as hereinbefore defined, with carbon disulphide and subsequently with an alkylating agent of general formula

(IV)

wherein

A and $R^7$ are as hereinbefore defined, with the proviso that $R^7$ does not represent an optionally substituted phenyl or naphthyl group if A denotes a single bond, and $Z^1$ denotes a leaving group, e.g. a halogen atom, such as the chlorine, bromine or iodine atom, an alkylsulfonyloxy group with 1 to 10 carbon atoms in the alkyl moiety, a phenylsulphonyloxy or naphthylsuphonyloxy group optionally mono-, di- or trisubstituted by chlorine or bromine atoms, by methyl or nitro groups, whilst the substituents may be identical or different. The reaction is appropriately carried out by first converting a compound of general formula (II) into the lithium salt in a suitable solvent, e.g. in tetrahydrofuran, dioxane, hexane or toluene, e.g. using n-butyllithium at a temperature of from −20 to −10° C., and then reacting it with carbon disulphide. Then a compound of general formula (IV) is added in a suitable solvent, e.g. in tetrahydrofuran, dimethylformamide, dimethylsulphide or a mixture thereof and the reaction is carried out at 20–60° C.

c) In order to prepare compounds of general formula (I) wherein E denotes a sulphinyl group:

Oxidation of a compound of general formula (I) wherein m, n, A, X, Y, and $R^1$ to $R^8$ are as hereinbefore defined and E denotes a sulphur atom, preferably with sodium metaperiodate.

The oxidation is conveniently carried out with one equivalent of the oxidising agent used, e.g. with sodium metaperiodate in aqueous methanol or ethanol at −15 to 25° C.

The compounds of general formula I prepared by the above methods can be purified and isolated by methods known per se, e.g. by crystallisation, distillation or chromatography.

Moreover, the compounds of general formula I obtained may optionally be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

The starting compounds of general formula II wherein E denotes a carbonyl group may be prepared by the methods described in DE 44 07 136 A1 (pp. 4–5).

The starting compounds of general formula II wherein E denotes a methylene group or the group —$C(R^9R^{10})$—, wherein $R^9$ denotes a hydrogen atom and $R^{10}$ together with the adjacent group $R^8$ denotes a carbon-carbon bond, can be prepared by the methods described in DE 44 07 138 A1 (5/1144) (pp. 7–8).

Compounds of general formula II wherein E denotes an oxygen or sulphur atom may be prepared by the following reaction plan:

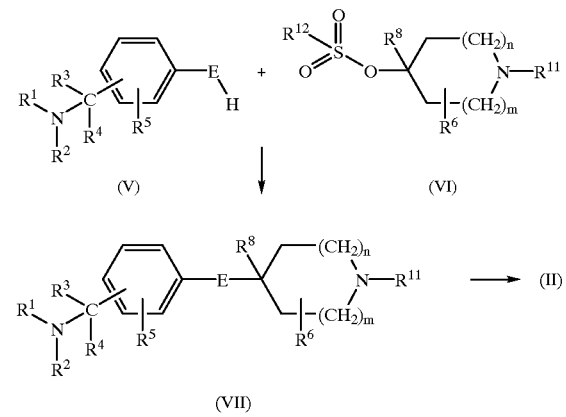

The reaction of a compound of formula V wherein $R^1$ to $R^5$ are as hereinbefore defined and E denotes an oxygen or sulphur atom with a compound of formula VI wherein m, n, $R^6$ and $R^8$ are as hereinbefore defined, $R^{11}$ denotes a protecting group, for example the tert.butyloxycarbonyl group, and $R^{12}$ denotes an alkyl group, yields a corresponding compound of formula VII which is converted by the cleaving of the protecting group $R^{11}$ into a compound of formula II.

Compounds of general formula II wherein E denotes a methylene group, an oxygen or sulphur atom, $R^3$ to $R^5$ and $R^8$ denote hydrogen atoms, $R^6$ denotes a hydrogen atom or an alkyl group and the phenyl group is 1,4-disubstituted may be prepared by the two methods shown in the following reaction plan:

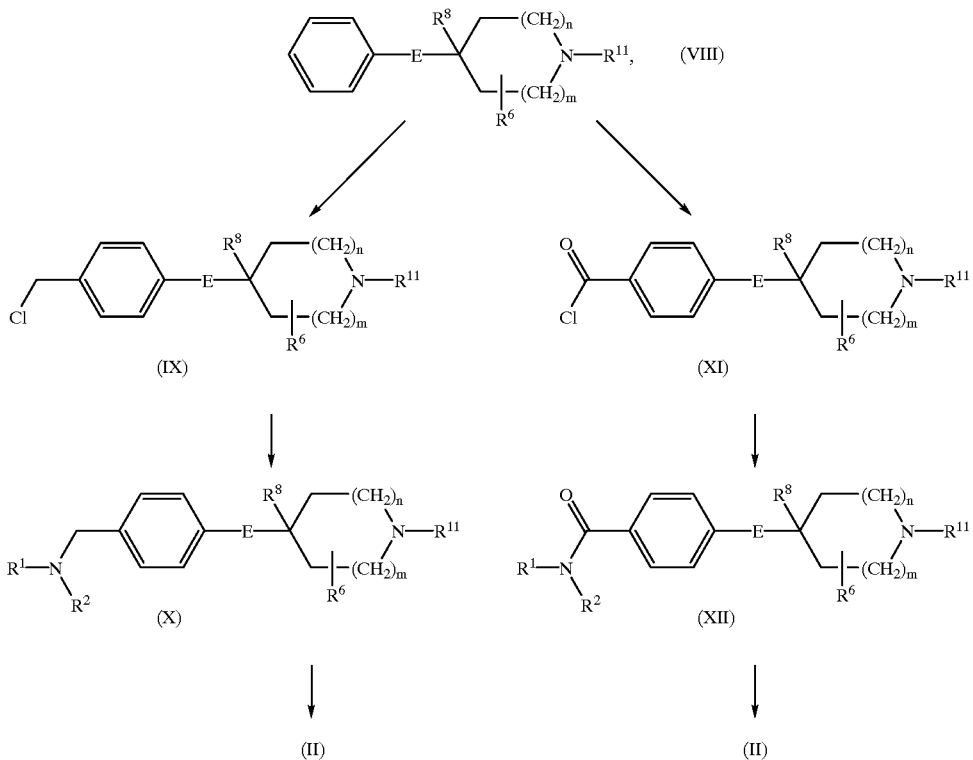

On the one hand a compound of formula VIII wherein $R^{11}$ denotes a protecting group, preferably a 2,2,2-trichloroethoxycarbonyl group, is converted by chloromethylation into a compound of formula IX. Aminolysis with an amine of formula $R^1R^2NH$ yields a compound of formula X which is converted by cleaving the protecting group into a compound of formula II.

On the other hand, a compound of formula VIII wherein $R^{11}$ denotes a protecting group, preferably the trifluoroacetyl group, may be converted by a Friedel-Crafts reaction with oxalylchloride in the presence of aluminium chloride into a compound of formula XI. Aminolysis with an amine of formula $R^1R^2NH$ yields a compound of formula XII which is converted by reduction with lithium aluminium hydride and cleaving of the protecting group into a compound of formula II.

Compounds of formula II wherein E denotes an oxygen or sulphur atom, $R^3$ to $R^5$ and $R^8$ denote hydrogen atoms, $R^6$ denotes a hydrogen atom or an alkyl group, may also be prepared by the following method:

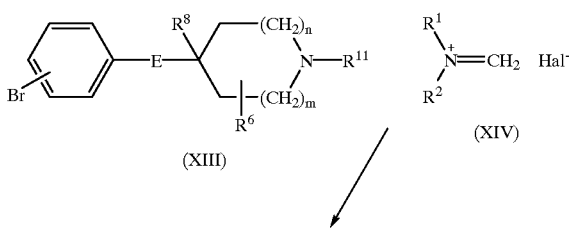

-continued

A compound of formula XIII wherein $R^{11}$ denotes a protecting group, preferably a trityl group, is first converted into the lithium compound and then reacted with a compound of formula XIV wherein Hal denotes a chlorine, bromine or iodine atom to form a compound of formula XV. Cleaving the protecting group yields a compound of formula II.

The compounds of general formula I have valuable biological properties. They are inhibitors of cholesterol biosynthesis, particularly inhibitors of the enzyme 2,3-epoxysqualene-lanosterol-cyclase. In view of their biological properties they are suitable for treating diseases in which cholesterol biosynthesis is implicated, particularly for the treatment and prophylaxis of hypercholesterolaemia, hyperlipoproteinaemia and hypertriglyceridaemia and the resultant atheroscleotic vascular changes with their sequelae such as coronary heart disease, cerebral ischaemia, Claudicatio intermittens, gangrene et al.

For treating these diseases the compounds of general formula I may be used either on their own for monotherapy or in conjunction with other cholesterol- or lipid-lowering substances, whilst the compounds may preferably be administered as an oral preparation, and optionally also in the form of suppositories as a rectal formulation. The following are possible combination partners:

bile acid-binding resins such as cholestyramine, cholestipol and others, compounds which inhibit cholesterol absorption such as e.g. sitosterol and neomycin, compounds which interfere with cholesterol biosynthesis by a mechanism other than inhibition of 2,3-epoxysqualene-lanosterol-cyclase such as e.g. HMG-CoA-reductase inhibitors such as lovastatin, simvastatin, pravastatin, fluvastatin, atorvastatin, cerivastatin and others, squalene-epoxidase inhibitors such as NB 598 and analogous compounds and squalene-synthetase inhibitors such as compounds from the class of the isoprenoid-(phosphinylmethyl) phosphonates and squalestatin.

Other possible combination partners still to be mentioned are the fibrates, such as clofibrate, bezafibrate, gemfibrozil and others, nicotinic acid, the derivatives and analogues thereof such as acipimox, and probucol.

Furthermore the compounds of general formula I are suitable for the treatment of diseases connected with excessive cell proliferation. Cholesterol is an essential ingredient of cells and must be present in sufficient quantities for cell proliferation, i.e. cell division. The inhibition of cell proliferation by inhibiting cholesterol biosynthesis is described with reference to the smooth muscle cells with the HMG-CoA-reductase inhibitor of the mevinolin type lovastatin, as mentioned hereinbefore.

Examples of diseases connected with excessive cell proliferation are primarily tumour diseases. In cell culture and in-vivo experiments it has been shown that the lowering of the serum cholesterol or intervention in cholesterol biosynthesis by means of HMG-CoA-reductase inhibitors reduces tumour growth (Lancet 339, 1154–1156 [1992]). The compounds of formula I according to the invention are therefore potentially suitable for treating tumour diseases on the basis of their inhibitory effect on cholesterol biosynthesis. They may be used on their own or in support of known therapeutic principles.

Other examples are hyperproliferative skin diseases such as psoriasis, basal cell carcinomas, plate epithelial carcinomas, keratosis and keratinisation disorders. The term "psoriasis" used here denotes a hyperproliferatively inflammatory skin disease which changes the regulatory mechanism of the skin. In particular, lesions are formed which contain primary and secondary changes in the proliferation in the epidermis, inflammatory reactions of the skin and the expression of regulatory molecules such as lymphokines and inflammatory factors. Psoriatic skin is morphologically characterised by an increased turnover of epidermis cells, thickened epidermis, abnormal keratinisation of inflammatory cell infiltrates into the dermis layer and polymorphonuclear leukocyte infiltration into the epidermis, causing an increase in the basal cell cycle. Additionally, hyperkeratotic and parakeratotic cells are present. The terms "keratosis", "basal cell carcinomas", "plate epithelial carcinomas" and "keratinisation disorders" relate to hyperproliferative skin diseases in which the regulating mechanism for the proliferation and differentiation of the skin cells has been disrupted.

The compounds of formula I are effective as antagonists of skin hyperproliferation, i.e. as agents which inhibit the hyperproliferation of human keratinocytes. The compounds are consequently suitable as agents for treating hyperproliferative skin diseases such as psoriasis, basal cell carcinomas, keratinisation disorders and keratosis. For treating these diseases the compounds of formula I may be administered either orally or topically, and may be used either on their own in the form of monotherapy or in combination with known active substances.

Hyperproliferative vascular diseases such as stenoses and vascular occlusions based on the proliferation of smooth muscle cells and caused by surgical procedures such as PTCA (percutaneous transluminal coronary angioplasty) or bypass operations should also be mentioned. As mentioned hereinbefore this cell proliferation is known to be suppressed by HMG-CoA-reductase inhibitors of the mevinoline type, such as lovastatin. In view of their inhibitory activity on cholesterol biosynthesis the compounds of general formula I are also suitable for the treatment and prophylaxis of these diseases, and may be used either on their own or in conjunction with known active substances such as intravenously administered heparin, preferably by oral administration.

Another possible use of the compounds of general formula I according to the invention is the prophylaxis and treatment of gallstone problems. The formation of gallstones is triggered by the cholesterol concentration in the bile exceeding the maximum solubility of the cholesterol in the bile fluid, causing the cholesterol to be precipitated in the form of gallstones. Lipid-lowering substances from the fibrate class lead to increased precipitation of neutral steroids through the bile and increase the tendency to form gallstones.

By contrast, cholesterol biosynthesis inhibitors such as lovastatin or pravastatin do not result in increased gallstone formation; on the contrary they may bring about a reduction in the cholesterol concentration in the bile and hence lower the so-called lithogenic index, a measurement of the probability of gallstone formation. This is described in Gut 31, 348–350 [1990] and in Z. Gastroenterol. 29, 242–245 [1991].

Moreover, the efficacy of lovastatin in dissolving gallstones, particularly in conjunction with ursodeoxycholic acid, is described in Gastroenterology 102, No. 4, Pt. 2, A 319 [1992]. In view of their mode of activity the compounds of general formula I are therefore also important in the prevention and treatment of gallstone problems. They may be used either on their own or in conjunction with known therapies such as, for example, treatment with ursodeoxycholic acid or shockwave lithotripsy, and are preferably administered orally.

Finally, the compounds of general formula I are suitable for the treatment of infections caused by pathogenic fungi such as e.g. Candida albicans, Aspergillus niger, Trichophyton mentagrophytes, Penicillium sp., Cladosporium sp. and others. As mentioned earlier, the end product of sterol biosynthesis in the fungal organism is not cholesterol, but ergosterol which is essential for the integrity and function of the fungal cell membranes. Inhibiting ergosterol biosynthesis therefore leads to growth disorders and possibly the death of the fungal organisms.

For treating mycoses the compounds of general formula I may be administered either orally or topically. They may be used either on their own or in conjunction with known antimycotic active substances, particularly with those which interfere in other stages of sterol biosynthesis, such as for example the squalene-epoxidase inhibitors terbinafine and naftifine or the lanosterol-14α-demethylase inhibitors of the azole type such as ketoconazole and fluconazole.

Another possible use of the compounds of general formula I is their application in poultry rearing. Lowering the cholesterol content of eggs by administering the HMG-CoA-reductase inhibitor lovastatin to laying hens has been described (FASEB Journal 4, A 533, Abstracts 1543 [1990]). The production of low-cholesterol eggs is of interest as the cholesterol loading of the body can be reduced without changing eating habits by means of eggs with a reduced cholesterol content. In view of their inhibitory activity on cholesterol biosynthesis the compounds of general formula I can also be used in poultry rearing to produce low-cholesterol eggs, the substances preferably being given to the hens as a feed additive.

The biological activity of compounds of general formula I was determined by the following methods:

I. Measuring the Inhibition of $^{14}$C-acetate Incorporation into the Steroids which can be Precipitated with Digitonin The inhibitory effect was investigated using the method described in J. Lipid. Res. 37, 148–157 [1996] at test concentrations of $10^{-8}$ and $10^{-9}$ mol/l.

By way of example, the test results for the following compounds (A) to (M) of general formula I and the comparison substances (U), (V) and (W) at these test concentrations are given:

(A) N-(benzylthio)thiocarbonyl-4-[4-(dimethylaminomethyl)phenylthio]piperidine-hydrochloride,
(B) N-(benzylthio)thiocarbonyl-4-[4-(dimethylaminomethyl)benzoyl]piperidine-hydrochloride,
(C) N-benzyloxycarbonyl-4-[4-(dimethylaminomethyl)phenylthio]piperidine-hydrochloride,
(D) N-(4-chlorophenoxy)carbonyl-4-[4-(dimethylaminomethyl)phenylthio]piperidine-hydrochloride,
(E) N-(benzylthio)thiocarbonyl-4-[4-(dimethylaminomethyl)benzyl]piperidine-hydrochloride,
(F) N-(benzylthio)thiocarbonyl-4-[4-(dimethylaminomethyl)benzyliden]piperidine-hydrochloride,
(G) N-(4-chlorophenoxy)thiocarbonyl-4-[4-(dimethylaminomethyl)benzyl]piperidine-hydrochloride,
(H) N-(4-chlorophenoxy)carbonyl-4-[4-(dimethylaminomethyl)benzyl]piperidine-hydrochloride,
(I) N-benzyloxycarbonyl-4-[4-(dimethylaminomethyl)benzyl]piperidine-hydrochloride,
(K) 4-[4-(dimethylaminomethyl)benzyl]-N-(4-methylphenoxy)carbonylpiperidine-hydrochloride,
(L) 4-[4-(dimethylaminomethyl)benzyl]-N-(4-methylphenoxy)thiocarbonylpiperidine-hydrochloride,
(M) 4-[4-(dimethylaminomethyl)benzyl]-N-(4-fluorphenoxy)carbonylpiperidine-hydrochloride,
(U) 1-(4-chlorobenzoyl) -4-[4-(2-oxazolin-2-yl)-benzylidene]-piperidine (EP-A-0 596 326, p. 16, compound A therein; J. Lipid. Res. 38, 564–575 [1997]),
(V) trans-N-(4-chlorobenzoyl)-N-methyl-[4-(4-dimethylamino)methyl)phenyl]cyclohexylamine (DE-A-44 38 020; J. Lipid. Res. 37, 148–157 [1996]) and
(W) trans-O-(p-tolylacetyl)-4-(4-dimethylaminomethylphenyl)cyclohexanol (WO 95/29148, p. 28, compound I therein).

The percentages by which the above compounds inhibit the $^{14}$C-acetate incorporation are shown in Table 1.

TABLE 1

| compound | $10^{-8}$ mol/l | $10^{-9}$ mol/l |
|---|---|---|
| (A) | −85 | −53 |
| (B) | −85 | −47 |
| (C) | −78 | −57 |

TABLE 1-continued

| compound | $10^{-8}$ mol/l | $10^{-9}$ mol/l |
|---|---|---|
| (D) | −86 | −55 |
| (E) | −87 | −47 |
| (F) | −84 | −45 |
| (G) | −83 | −56 |
| (H) | −80 | −45 |
| (I) | −85 | −47 |
| (K) | −82 | −49 |
| (L) | −88 | −64 |
| (M) | −84 | −59 |
| (U) | −54 | −07 |
| (V) | −59 | −23 |
| (W) | −72 | −21 |

The $IC_{50}$ values of compounds H, I, K and M were determined. These are given together with the $IC_{50}$ values of compounds U, V and W in Table 2.

TABLE 2

| Compound | $IC_{50}$ (nmol/l) |
|---|---|
| (H) | 0.8 |
| (I) | 1.2 |
| (K) | 1.4 |
| (M) | 1.5 |
| (U) | 5.5 |
| (V) | 3.8 |
| (W) | 9.6 |

Table 2 shows that the compounds according to the invention are significantly superior to the comparison substances described earlier.

II. Measuring the In-vivo Activity in the Rat after Oral Administration

Inhibiting the enzyme 2,3-epoxysqualene-lanosterol-cyclase causes an increase in the 2,3-epoxisqualene levels in the liver and plasma. The quantity of 2,3-epoxysqualene formed therefore serves as a direct measurement of the potency on the animal as a whole. The amounts were determined using the method described in J. Lipid. Res. 38, 564–575, [1997] after t=3 or 8 hours after administration of the substance in concentrations of c=0.01, 0.03, 0.1, 0.3 and 1.0 mg/kg. Table 3 which follows gives the results obtained for the abovementioned substances A, B, C, D, E, G, H, I and K by way of example.

TABLE 3

| 2,3-epoxysqualene concentration [µg/g] In the liver (rat) | | | | | | | | | |
|---|---|---|---|---|---|---|---|---|---|
| c [mg/kg] | 0.01 | | 0.03 | | 0.1 | | 0.3 | | 1.0 | |
| t [h] | 3 | 8 | 3 | 8 | 3 | 8 | 3 | 8 | 3 | 8 |
| A | | | | | | | 2.0 | 1.2 | 9.3 | 9.8 |
| B | | | | | | | 4.5 | 5.8 | 39.2 | 42.0 |
| C | 0.6 | 3.0 | | | 0.5 | 1.3 | 0.5 | 1.8 | 3.8 | 2.0 |
| D | 1.3 | 1.0 | | | 1.4 | 1.8 | | | | |
| E | 0.9 | 1.0 | | | 5.6 | 4.4 | | | | |
| G | | | | | 10.3 | 11.5 | | | 87.4 | 134.2 |
| H | | | | | 1.0 | 0.8 | | | 56.3 | 20.7 |
| I | | | | | 1.0 | | | | 26.1 | 10.0 |
| K | | | | | 0.4 | 0.4 | | | 24.0 | 5.5 |

In the control animals there were no measurable 2,3-epoxisqualene levels under these conditions.

III. Lipid Reduction in the Normolipaemic Golden Hamster

This was determined using the method described in J. Lipid. Res. 38, 564–575, (1997). At the end of the experiment the total cholesterol, β-lipoprotein-cholesterol and HDL-cholesterol were determined and compared with the values of a control group which were fed without any test substance.

The lipid-lowering activity of the abovementioned compound H was tested.

The results are shown in Table 4.

TABLE 4

| Comp. | Dose [mg/kg/day] | Total cholesterol [%] | β-Lipoprotein-cholesterol [%] | HDL-cholesterol [%] |
|---|---|---|---|---|
| H | 6.5 | −8.3 | −13.0 | −3.4 |
|   | 19.9 | −11.0 | −13.2 | −8.2 |
|   | 62.3 | −32.1 | −33.7 | −28.5 |
| I | 47.1 | −23.1 | −32.9 | −17.6 |
| K | 54.2 | −6.8 | −21.2 | 2.3 |
| M | 57.5 | −26.8 | −31.6 | −20.4 |

Under these conditions the compounds exhibited no toxic effects.

IV. Determining the Fungistatic Activity

The fungistatic activity was determined by the series dilution test (microtitre system). Sabouraud broth was used as the nutrient medium. The inoculum amounted to about $10^4$ to $10^5$ CFU/ml (CFU=colony-forming units); the incubation period was 2 to 4 days at 26° C.

The lowest concentration which allows no visible growth (minimum inhibitory concentration MIC) was determined.

The abovementioned compounds A, B, D, E, F, H, I, K, L and M were tested. The results are assembled in the following Table 5. The MIC is given in μg/ml.

The following test pathogens were used:

| Test pathogen | Abbreviation |
|---|---|
| Cand. albicans ATCC 10231 | Cand. |
| Sacch. carlsbergensis ATCC 9080 | Sacc. |
| Rhod. rubra 49 | Rhod. |
| Asp. niger ATCC 16404 | Asp. |
| Trich. mentagrophytes ATCC 9129 | Trich. |
| Pen. notatum CBS 19746 | Pen. |

TABLE 5

| Test comp. | MHK [μg/ml] | | | | | |
|---|---|---|---|---|---|---|
|   | Cand. | Sacc. | Rhod. | Asp. | Trich. | Pen. |
| A | 16 | 8 | 16 | 8 | 1 | 4 |
| B | 64 | 32 | 16 | 32 | 2 | 8 |
| D | 64 | 128 | 64 | 256 | 16 | 128 |
| E | 16 | 16 | 4 | 8 | 1 | 1 |
| F | 16 | 16 | 4 | 8 | 2 | 4 |
| H | 64 | 128 | 16 | 32 | 1 | 64 |
| I | 256 | 512 | 64 | 64 | 4 | 128 |
| K | 64 | 512 | 64 | 64 | 8 | 256 |
| L | 32 | 64 | 8 | 64 | 1 | 32 |
| M | 128 | 512 | 32 | 64 | 2 | 512 |

For pharmaceutical use the compounds of general formula I may be incorporated in the conventional pharmaceutical preparations for oral, rectal and topical administration in a manner known per se.

Formulations for oral administration include for example plain and coated tablets and capsules. For rectal administration suppositories may be used. The daily dose is between 0.1 and 200 mg for a person with a body weight of 60 kg, but the preferred daily dose is from 1 to 100 mg for a person weighing 60 kg. The daily dose is preferably divided into 1 to 3 individual doses.

For topical application the compounds may be administered in preparations containing about 1 to 1000 mg, particularly 10 to 300 mg of active substance per day. The daily dose is preferably divided into 1 to 3 individual doses.

Topical formulations include gels, creams, lotions, ointments, powders, aerosols and other conventional formulations for applying medicaments to the skin. The amount of active substance for topical use is 1 to 50 mg per gram of formulation, but preferably 5 to 20 mg per gram of formulation. Apart from application to the skin the topical formulations of the present invention may also be used in the treatment of mucous membranes accessible to topical treatment. For example, the topical formulations may be applied to the mucous membranes of the mouth, lower colon, etc.

For use in poultry rearing for the production of low-cholesterol eggs the active substances of general formula I are administered to the animals by the usual methods as an additive to suitable feedstuffs. The concentration of the active substances in the finished feed is normally 0.01 to 1%, but preferably 0.05 to 0.5%.

The active substances may be added to the feed as they are. Thus, the feeds for laying hens according to the invention contain, in addition to the active substance and optionally a conventional vitamin-mineral mixture, maize, soya bean flour, meat meal, edible fat and soya oil, for example. To this feed is added one of the abovementioned compounds of formula I as active substance in a concentration of from 0.01 to 1%, but preferably 0.05 to 0.5%.

The following Examples serve to illustrate the invention more fully. The $R_f$ values given were determined on ready-made plates obtained from E.Merck of Darmstadt on:

a) aluminium oxide F-254 (type E)

b) silica gel 60 F-254

EXAMPLES OF THE PREPARATION OF THE STARTING MATERIALS

Example A

4-[4-(Dimethylaminomethyl)phenylthio]piperidine

To a solution of 7.18 g (71 mmol) of 4-hydroxypiperidine in 100 ml dimethylformamide are added first 19.6 g (142 mmol) of powdered potassium carbonate and then 19.8 9 (71 mmol) of tritylchloride. The mixture is stirred for 22 hours at ambient temperature, diluted with ethyl acetate to twice the volume, washed with water and saturated saline solution, dried with magnesium sulphate and concentrated by evaporation. The residue is recrystallised from ethyl acetate/petroleum ether (1:4, v:v). 17.65 g (72.4% of theory) of 4-hydroxy-N-tritylpiperidine are obtained as colourless crystals, melting point 157–158° C.

5.77 g of this product are dissolved in 60 ml methylene chloride, 2.6 g of methanesulphonic acid chloride are added and 3.4 g of triethylamine are slowly added dropwise. The mixture is stirred for 1 hour at 0° C., diluted with ether, washed with ice water (4×), dried with magnesium sulphate and concentrated by evaporation. 7.58 g of 4-methanesulphonyloxy-N-tritylpiperidine is obtained as a colourless foam.

The product is dissolved in 30 ml of tetrahydrofuran and added dropwise to a solution of the sodium salt of 4-bromothiophenol (prepared from 3.18 g of 4-bromothiophenol and 0.81 g of 55% sodium hydride in 35 ml tetrahydrofuran). It is heated to boiling for 1 hour, cooled, then taken up in ethyl acetate, washed with water and saturated saline solution, dried with magnesium sulphate and concentrated by evaporation. 5.28 g of 4-(4-bromophenylthio)-N-tritylpiperidine are obtained as colourless crystals, melting point 174–175° C.

2.57 g (5 mmol) of this product are dissolved in 30 ml tetrahydrofuran and at −70° C. 4 ml (6.4 mmol) of a 1.6-molar solution of n-butyllithium in n-hexane are added dropwise. After 1.5 hours at -70° C., 1.1 g (6.4 mmol) of N,N-dimethyl-methyleneimmonium-iodide are added, the cooling bath is removed and the mixture is stirred overnight. The solvent is evaporated, the residue is triturated with water and extracted with ethyl acetate. The organic phase is dried with magnesium sulphate, concentrated by evaporation and the residue is purified by column chromatography (aluminium oxide, ethyl acetate/petroleum ether=1:10, v:v). 0.9 g 4-[4-(dimethylaminomethyl)phenylthio]-N-tritylpiperidine are obtained as colourless crystals, melting point 163° C.

This product is dissolved in 30 ml methylene chloride and 10 ml ethereal hydrochloric acid are added. After 1 hour at ambient temperature the mixture is concentrated by evaporation, combined with ether and the precipitate is suction filtered. This is dissolved in a little water, ether is added and the mixture is adjusted to pH 11 with 6N-sodium hydroxide solution. The ether phase is separated off, the aqueous phase is again extracted with ether and the combined extracts are dried with magnesium sulphate. 500 mg of 4-[4-(dimethylaminomethyl)phenylthio]piperidine are obtained as colourless crystals, melting point 52° C.

Example B

4-[4-(Piperidinomethyl)phenylthio]piperidine 10.1 g (0.1 mol) of 4-hydroxypiperidine and 11 g (0.11 mol) of triethylamine are placed in 200 ml ethyl acetate and 250 ml tetrahydrofuran and a solution of 23.3 g (0.11 mol) of 2,2,2-trichloroethyl chloroformate is added dropwise at 0–4° C. The mixture is stirred for 1 hour at 0° C. and for 1 hour at ambient temperature. The precipitate is suction filtered, the filtrate is combined at −12 to −14° C. with 12 g (0.105 mol) of methanesulphonic acid chloride and at −8 to −12° C. 12 g (0.12 mol) of triethylamine in 50 ml tetrahydrofuran are added dropwise. It is stirred for 40 minutes at −10° C., the cooling bath is removed and the mixture is stirred for 30 minutes. After washing with water and saturated saline solution it is dried with magnesium sulphate, concentrated by evaporation, the residue is triturated with diisopropylether and suction filtered. 32.4 g (91.5% of theory) of 4-methanesulphonyloxy-N-2,2,2-trichlorethoxycarbonylpiperidine are obtained as colourless crystals, melting point 93° C.

17.7 g (50 mmol) of this product in 30 ml dimethylformamide are added dropwise at ambient temperature to a solution of potassium thiophenoxide (prepared from 6 g thiophenol and 6.2 g potassium-tert. butoxide in 50 ml dimethylformamide at 20–60° C.). The jelly formed is combined with 100 ml dimethylformamide, heated to 60° C. and after the addition of 30 ml methanol left to stand overnight at ambient temperature. After the addition of 800 ml water the mixture is extracted with ether, the ether extract is washed with water, dried with magnesium sulphate and concentrated by evaporation. After purification by column chromatography (silica gel, petroleum ether/ethyl acetate= 5:1, v:v) 11 g (64.3% of theory) of 4-phenylthio-N-2,2,2-trichlorethoxycarbonylpiperidine are obtained as a colourless oil.

9 g (25 mmol) of this product, 6 g paraformaldehyde and 5.6 g (42 mmol) of zinc chloride are placed in 300 ml methylene chloride. At 20–22° C., hydrogen chloride is introduced for 30 minutes. After one hour hydrogen chloride is again piped in for 10 minutes and then the mixture is stirred overnight. The reaction mixture is stirred into 300 ml of a 1-molar disodium hydrogen phosphate solution, the methylene chloride phase is separated off and the aqueous phase extracted with methylene chloride. The organic phases are combined, washed with water, dried with magnesium sulphate and concentrated by evaporation. After purification by column chromatography (silica gel, ethyl acetate/ petroleum ether=1:10, v:v) 4.5 g (43.2% of theory) of 4-[4-(chloromethyl)phenylthio]-N-2,2,2-trichloroethoxycarbonylpiperidine are obtained as a colourless oil.

2.1 g (5 mmol) of this product and 1.3 g (15 mmol) of piperidine are refluxed in 10 ml tetrahydrofuran and 10 ml ethanol for 2.5 hours. After evaporation, the residue is triturated with water and extracted with ether. The ether phase is washed with water, dried with magnesium sulphate and concentrated by evaporation. 2.5 g of 4-[4-(piperidinomethyl)phenylthio]-2,2,2-trichloroethoxycarbonylpiperidine are obtained as a crude product.

2.4 g of this product are dissolved in 3.5 ml acetic acid and 18 ml of water and 5 g of zinc powder are added (vigorous foaming). The mixture is stirred for 20 hours at ambient temperature and for 1 hour at 500° C. After the addition of 20 ml of water a layer of 100 ml ether is added, the mixture is made strongly alkaline with 6N-sodium hydroxide solution and stirred for 20 minutes. The ether is separated off and the aqueous phase extracted 3× with ether. The combined extracts are dried with magnesium sulphate and concentrated by evaporation. 1.3 g of 4-[4-(piperidinomethyl) phenylthio]-piperidine are obtained as a colourless powder.

$R_f$ value: 0.69 (aluminium oxide, methylene chloride/ methanol=10:1, v:v).

Example C

4-[4-(dimethylaminomethyl)benzyl]piperidine 100 g (0.57 mol) of 4-benzylpiperidine in 220 ml methanol are combined with 88 g (0.68 mol) of methyl trifluoroacetate at 20 to 35° C. After 2 hours the mixture is concentrated by evaporation. After crystallisation of the residue from petroleum ether, 117 g (76% of theory) of 4-benzyl-N-trifluoroacetylpiperidine are obtained as colourless crystals.

113 g (0.848 mol) of aluminium chloride in 600 ml of dichloroethane are combined with 114 g (0.9 mol) of oxalylchloride. At −4 to +4° C. 114 g of the above product are added dropwise to 300 ml of dichloroethane (development of gas). The mixture is stirred for 2.5 hours at ambient temperature and then at −25° C. 300 ml of a 40% aqueous dimethylamine solution is added quickly (temperature rises to 35° C.). The jelly formed is diluted with 100 ml dichloroethane, stirred for 20 minutes and diluted with chloroform to improve phase separation. It is washed with water, 2N sodium hydroxide solution, water, 2N hydrochloric acid and again with water. The organic phase is dried with magnesium sulphate, concentrated by evaporation and the residue triturated with ether. 111 g (80% of theory) of 4-[4-(dimethylaminocarbonyl)benzyl]-N-trifluoracetylpiperidine are obtained as colourless crystals.

64 g of this product in 350 ml tetrahydrofuran are added dropwise at 0 to 3° C. to 70 ml of a 20% solution of lithium aluminium hydride in ether, diluted with 250 ml ether. This is stirred for 20 minutes at 0° C. and then refluxed for 1 hour. At 0 to 15° C. 40 ml 4N-sodium hydroxide solution are added dropwise (vigorous foaming), stirred for 30 minutes at ambient temperature, suction filtered and the filter residue is washed with ether. The combined ether phases are dried with magnesium sulphate and concentrated by evaporation. 46 g (99% of theory) of 4-[4-(dimethylaminomethyl)benzyl] piperidine are obtained as a colourless, slowly crystallising oil.

$R_f$ value: 0.56 (aluminium oxide, methylene chloride/methanol=10:1, v:v).

EXAMPLES OF THE PREPARATION OF THE END PRODUCTS

Example 1

N-(benzylthio)thiocarbonyl-4-[4-(dimethylaminomethyl)phenylthio]piperidine-hydrochloride A mixture of 237 mg (0.83 mmol) of 4-[4-(dimethylaminomethyl)phenylthio]piperidine, 200 mg (2 mmol) of triethylamine and 1 ml ethanol are combined at ambient temperature with 150 mg (2 mmol) of carbon disulphide. The precipitate formed is dissolved by the addition of 1 ml of triethylamine and 2.5 ml of dimethylformamide. After 1 hour at ambient temperature 160 mg (0.94 mmol) of benzylbromide are added, it is stirred overnight at ambient temperature and then heated to 60° C. for 3 hours. After the addition of 50 ml water the mixture is extracted with ethyl acetate, the organic phase is dried with magnesium sulphate and concentrated by evaporation. After purification of the residue by column chromatography (aluminium oxide, petroleum ether/ethyl acetate=4:1, v:v) 210 mg of the title compound are obtained as a colourless oil, which is converted into the hydrochloride with ethereal hydrochloric acid. $R_f$ value of the free base: 0.83 (aluminium oxide, ethyl acetate/petroleum ether=3:1, v:v).

$^1$H-NMR spectrum (200 MHz,DMSO-d$_6$), signals at ppm: 1.4–1.6 (m, 2H), 2.0–2.15 (m, 2H), 2.55 (d, 6H), 3.5–3.65 (t, 2H), 3.7–3.85 (m, 1H), 4.2 (d, 2H), 4.3–4.4 (m, 1H), 4.5 (s, 2H), 4.95–5.15 (m, 1H), 7.2–7.6 (m, 9H)

The following are obtained analogously:
(1) N-(benzylthio)thiocarbonyl-4-[4-(dimethylaminomethyl)benzoyl]piperidine-hydrochloride,
   from 4-[4-(dimethylaminomethyl)benzoyl]piperidine and benzylbromide; colourless powder; $R_f$ value of the free base: 0.65 (aluminium oxide, ethyl acetate)
(2) N-(benzylthio)thiocarbonyl-4-[4-(dimethylaminomethyl)benzylidene]piperidine-hydrochloride,
   from 4-[4-(dimethylaminomethyl)benzylidene]piperidine and benzylbromide; colourless powder; melting point: 190° C.
(3) N-(benzylthio)thiocarbonyl-4-[4-(dimethylaminomethyl)benzyl]piperidine-hydrochloride,
   from 4-[4-(dimethylaminomethyl)benzyl]piperidine and benzylbromide; colourless powder; $R_f$ value of the free base: 0.26 (aluminium oxide, petroleum ether/ethyl acetate=10:1, v:v)

Example 2

N-benzyloxycarbonyl-4-[4-(dimethylaminomethyl)phenylthio]piperidine 250 mg (1 mmol) of 4-[4-(dimethylaminomethyl)phenylthio]piperidine in 20 ml tetrahydrofuran are combined with 2 ml 2N sodium hydroxide solution and 5 ml water. At ambient temperature 200 mg (1.2 mmol) of benzyl chloroformate in 5 ml tetrahydrofuran are slowly added dropwise. After 1.5 hours at ambient temperature some benzyl chloroformate and sodium hydroxide solution are again added. After the addition of 100 ml ether the mixture is washed with saturated saline solution, the organic phase is dried with magnesium sulphate and concentrated by evaporation. The product obtained after purification by column chromatography (aluminium oxide, petroleum ether/ethyl acetate=4:1, v:v) is converted into the hydrochloride with ethereal hydrochloric acid. 190 mg (45.1% of theory) of the title compound are obtained as a colourless powder, melting point 144° C.

$^1$H-NMR spectrum (200 MHz,DMSO-d$_6$), signals at ppm: 1.3–1.5 (m, 2H), 1.85–2.0 (m, 2H), 2.65 (s, 6H), 2.95–3.15 (t, 2H), 3.5–3.65 (m, 1H), 3.8–4.0 (m, 2H), 4.2 (s, 2H), 5.05 (s, 2H), 7.3–7.6 (m, 9H)

The following are obtained analogously:
(1) N-(4-chlorophenylthio)thiocarbonyl-4-[4-(dimethylaminomethyl)phenylthio]piperidine-hydrochloride,
   from 4-[4-(dimethylaminomethyl)phenylthio]piperidine and 4-chlorophenyl chlorodithioformate; colourless powder; melting point: 178° C.
(2) 4-[4-(dimethylaminomethyl)phenylthio]-N-phenoxycarbonylpiperidine-hydrochloride, from 4-[4-(dimethylaminomethyl)phenylthio]piperidine and phenyl chloroformate; colourless powder; melting point: 161° C.
(3) N-(4-chlorophenoxy)carbonyl-4-[4-(dimethylaminomethyl)phenylthio]piperidine-hydrochloride,
   from 4-[4-(dimethylaminomethyl)phenylthio]piperidine and 4-chlorophenyl chloroformate; colourless powder; melting point:169° C.
(4) 4-[4-(dimethylaminomethyl)phenylthio]-N-(phenylthio)thiocarbonylpiperidine-hydrochloride,
   from 4-[4-(dimethylaminomethyl)phenylthio]piperidine and phenyl chlorodithioformate; colourless powder; $R_f$ value of the free base: 0.57 (aluminium oxide, petroleum ether/ethyl acetate=4:1, v:v)
(5) N-4-(4-chlorophenoxy)thiocarbonyl-4-[4-(dimethylaminomethyl)benzyl]piperidine-hydrochloride,
   from 4-[4-(dimethylaminomethyl)benzyl]piperidine and 0-4-chlorophenyl chlorothioformate; colourless powder; melting point :150° C.
(6) N-(4-chlorophenoxy)carbonyl-4-[4-(dimethylaminomethyl)benzyl]piperidine,
   from 4-[4-(dimethylaminomethyl)benzyl]piperidine and 4-chlorophenyl chloroformate; melting point of the free base: 104° C.;
The hydrochloride was obtained by treating with hydrochloric acid. Colourless powder; melting point: 156° C.;

The methanesulphonate was obtained by treating the free base with methanesulphonic acid in an ethyl acetate-ether mixture. Colourless powder; melting point: 152° C.

The tartrate was obtained by treating the free base with L-tartaric acid in a methanol-ethyl acetate mixture. Colourless powder; melting point: 147° C.

(7) N-(4-chlorophenylthio)carbonyl-4-[4-(dimethylaminomethyl)benzyl]piperidine-hydrochloride,
from 4-[4-(dimethylaminomethyl)benzyl]piperidine and S-4-chlorophenyl chlorothioformate; colourless powder; melting point: 190–191° C.

(8) N-benzyloxycarbonyl-4-[4-(piperidinomethyl)phenylthio]piperidine-hydrochloride,
from 4-[4-(piperidinomethyl)phenylthio]piperidine and benzyl chloroformate; colourless powder; melting point: 186° C.

(9) N-phenoxycarbonyl-4-[4-(piperidinomethyl)phenylthio]piperidine-hydrochloride,
from 4-[4-(piperidinomethyl)phenylthio]piperidine and phenyl chloroformate; colourless powder; melting point: 204° C.

(10) N-4-chlorophenoxycarbonyl-4-[4-(piperidinomethyl)phenylthio]piperidine-hydrochloride,
from 4-[4-(piperidinomethyl)phenylthio]piperidine and 4-chlorophenyl chloroformate; colourless powder; melting point: 182° C.

(11) N-benzyloxycarbonyl-4-[4-(dimethylaminomethyl)benzyl]piperidine,
from 4-[4-(dimethylaminomethyl)benzyl]piperidine and benzyl chloroformate; melting point of the free base: 63° C.;

The hydrochloride was obtained by treating with hydrochloric acid. Colourless powder; melting point: 132° C.;

The methanesulphonate was obtained by treating the free base with methanesulphonic acid in an ethyl acetate-ether mixture. Colourless powder; melting point: 140° C.

The tartrate was obtained by treating the free base with L-tartaric acid in a methanol-ethyl acetate mixture. Colourless powder; melting point: 125° C.

(12) 4-[4-(dimethylaminomethyl)benzyl]-N-(4-methylphenoxy)carbonylpiperidine,
from 4-[4-(dimethylaminomethyl)benzyl]piperidine and 4-methylphenyl chloroformate; melting point of the free base: 80° C.;

The hydrochloride was obtained by treating with hydrochloric acid. Colourless powder; melting point: 185° C.;

The methanesulphonate was obtained by treating the free base with methanesulphonic acid in an ethyl acetate-ether mixture. Colourless powder; melting point: 165° C.

The tartrate was obtained by treating the free base with L-tartaric acid in a methanol-ethyl acetate mixture. Colourless powder; melting point: 162° C.

(13) 4-[4-(dimethylaminomethyl)benzyl]-N-(4-methylphenoxy)thiocarbonylpiperidine-hydrochloride,
from 4-[4-(dimethylaminomethyl)benzyl]piperidine and 0-4-methylphenyl chlorothioformate; colourless powder; melting point: 184° C.

(14) 4-[4-(dimethylaminomethyl)benzyl]-N-(4-fluorphenoxy)carbonylpiperidine-hydrochloride,
from 4-[4-(dimethylaminomethyl)benzyl]piperidine and 4-fluorphenyl chloroformate; colourless powder;

$R_f$ value of the free base: 0.61 (aluminium oxide, petroleum ether/ethyl acetate=6:1, v:v)

Example 3

N-benzyloxycarbonyl-4-[4-(dimethylaminomethyl)phenylsulphinyl]piperidine-hydrochloride 90.7 mg (0.215 mmol) of N-benzyloxy-4-[4-(dimethylaminomethyl)phenylthio]piperidine hydrochloride are dissolved in a mixture of 1 ml methanol and 1 ml water and first 18.6 mg (0.226 mmol) of anhydrous sodium acetate and then 48.4 mg (0.226 mmol) of sodium metaperiodate are added. The mixture is stirred for 6 hours at ambient temperature, diluted with water, covered with ethyl acetate and saturated with sodium carbonate. The organic phase is separated off, the aqueous phase extracted with ethyl acetate, the organic phases are combined, washed with saturated saline solution, dried with magnesium sulphate and concentrated by evaporation. The residue is dissolved in a little methylene chloride, combined with ethereal hydrochloric acid and the solvent is evaporated. The residue is triturated with ether, the solvent is evaporated and the residue is dried in a high vacuum. 85 mg (90.5% of theory) of the title compound are obtained as a colourless powder.

$R_f$ value of the free base: 0.43 (aluminium oxide, ethyl acetate/petroleum ether=1:1, v:v).

$^1$H-NMR spectrum (200 MHz, DMSO-$d_6$), signals at ppm: 1.3–1.6 (m, 3H), 1.8–2.0 (m, 1H), 2.65 (s, 6H), 2.7–3.1 (m, 3H), 3.95–4.15 (t, 2H), 4.35 (s, 2H), 5.05 (s, 2H), 7.3 (s, 5H), 7.65–7.85 (q, 4H)

The following is obtained analogously:
(1) 4-[4-(dimethylaminomethyl)phenylsulphinyl]-N-phenoxycarbonylpiperidine-hydrochloride,
from 4-[4-(dimethylaminomethyl)phenylthio]-N-phenoxycarbonylpiperidine-hydrochloride and sodium metaperiodate; colourless powder; $R_f$ value of the free base: 0.4 (aluminium oxide, ethyl acetate/petroleum ether=1:1, v:v).

What is claimed is:

1. A compound of the formula I:

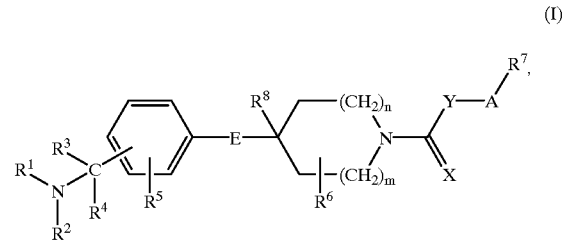

wherein:
m is 0 or 1;
n is 1 or 2;
A is a single bond, a straight-chained or branched $C_{1-8}$-alkylene group, or a $C_{2-8}$-alkenylene or $C_{2-8}$-alkynylene group, wherein an unsaturated group is not directly bound to the group Y;
X is an oxygen or sulfur atom;
Y is an oxygen or sulfur atom;
$R^1$ is a straight-chained or branched $C_{1-6}$-alkyl group, a $C_{1-4}$-alkenyl group, or a $C_{1-4}$-alkynyl group, wherein the multiple bond is isolated from the nitrogen-carbon bond;
$R^2$ is a straight-chained or branched $C_{1-6}$-alkyl group, a $C_{1-4}$-alkenyl group, or a $C_{1-4}$-alkynyl group, wherein the multiple bond is isolated from the nitrogen-carbon bond; or
$R^1$ and $R^2$ together with the nitrogen atom is a 5- to 7-membered, saturated heterocyclic ring, wherein a methylene group isolated from the nitrogen atom may be replaced by an oxygen or sulfur atom or by an —NH— or —N(alkyl)-group;

R³ to R⁶, which may be identical or different, are hydrogen atoms or alkyl groups;

R⁷ is a $C_{3-7}$-cycloalkyl group, a phenyl or naphthyl group optionally substituted by one or two halogen atoms or by an alkyl, alkoxy, trifluoromethyl, or cyano group;

E is an oxygen or sulfur atom, a methylene, carbonyl, or sulfinyl group; and

R⁸ is a hydrogen atom; or

E is the group —C(R⁹R¹⁰)—, wherein
R⁹ is a hydrogen atom, and
R¹⁰ together with the adjacent group R⁸ is a carbon-carbon bond, wherein, unless otherwise stated, alkyl groups contained in the groups mentioned above contain 1 to 3 carbon atoms and a halogen atom mentioned above is a fluorine, chlorine, or bromine atom, and wherein n+m is 2, or a pharmaceutically acceptable salt thereof.

2. The compound of formula I according to claim 1, wherein:

m is 1;

n is 1;

A is a single bond, a straight-chained or branched $C_{1-4}$-alkylene group, or a $C_{2-4}$-alkenylene group, wherein an unsaturated group is not directly bound to the group Y;

X is an oxygen or sulfur atom;

Y is an oxygen or sulfur atom;

R¹ is a straight-chained or branched $C_{1-6}$-alkyl group, or an allyl or propargyl group, wherein the multiple bond is isolated from the nitrogen-carbon bond;

R² is a straight-chained or branched $C_{1-6}$-alkyl group, or an allyl or propargyl group, wherein the multiple bond is isolated from the nitrogen-carbon bond;

R¹ and R² together with the nitrogen atom are a 5- to 7-membered, saturated heterocyclic ring wherein a methylene group isolated from the nitrogen atom may be replaced by an oxygen or sulfur atom;

R³ to R⁶, which may be identical or different, are hydrogen atoms or methyl groups;

R⁷ is a $C_{3-6}$-cycloalkyl group, or a phenyl or naphthyl group optionally substituted by one or two halogen atoms or by an alkyl, alkoxy, trifluoromethyl, or cyano group;

E is a sulfur atom, or a methylene, carbonyl, or sulfinyl group; and

R⁸ is a hydrogen atom; or

E is the group —C(R⁹R¹⁰)—, wherein
R⁹ is a hydrogen atom, and
R¹⁰ together with the adjacent group R⁸ is a carbon-carbon bond, wherein, unless otherwise stated, alkyl groups contained in the groups mentioned above each contain 1 to 3 carbon atoms and a halogen atom mentioned above is a fluorine, chlorine, or bromine atom, or a pharmaceutically acceptable salt thereof.

3. The compound of the formula I according to claim 1, wherein:

m is 1;

n is 1;

A is a single bond or a straight-chained or branched $C_{1-3}$ alkylene group;

X is an oxygen or sulfur atom;

Y is an oxygen or sulfur atom;

R¹ is a straight-chained or branched $C_{1-3}$-alkyl group;

R² is a straight-chained or branched $C_{1-3}$-alkyl group; or

R¹ and R² together with the nitrogen atom are a piperidino or morpholino group;

R³ to R⁶ are hydrogen atoms;

R⁷ is a cyclohexyl group or a phenyl group optionally substituted by a halogen atom or by an alkyl, alkoxy, or trifluoromethyl group;

E is a sulfur atom, or a methylene group, a carbonyl, or sulfinyl group; and

R⁸ is a hydrogen atom, or

E is the group —C(R⁹R¹⁰)—, wherein
R⁹ is a hydrogen atom, and
R¹⁰ together with the adjacent group R⁸ is a carbon-carbon bond, or a pharmaceutically acceptable salt thereof.

4. The compound of the formula I according to claim 1, wherein m is 1;

n is 1;

A is a single bond or a methylene group;

X is an oxygen or sulfur atom;

Y is an oxygen or sulfur atom;

R¹ and R² each are a methyl group;

R³ to R⁶ are hydrogen atoms;

R⁷ is a phenyl group optionally substituted by a fluorine or chlorine atom or by a methyl group;

E is a sulfur atom, or a methylene or carbonyl group; and

R⁸ is a hydrogen atom, or

E is the group —C(R⁹R¹⁰)—, wherein
R⁹ is a hydrogen atom, and
R¹⁰ together with the adjacent group R⁸ is a carbon-carbon bond, or a pharmaceutically acceptable salt thereof.

5. The compound selected from the group consisting of:

(a) N-(benzylthio)thiocarbonyl-4-[4-(dimethylaminomethyl)phenylthio]piperidine;

(b) N-(benzylthio)thiocarbonyl-4-[4-(dimethylaminomethyl)benzoyl]piperidine;

(c) N-benzyloxycarbonyl-4-[4-(dimethylaminomethyl)phenylthio]piperidine;

(d) N-(4-chlorophenoxy)carbonyl-4-[4-(dimethylaminomethyl)phenylthio]piperidine;

(e) N-(benzylthio)thiocarbonyl-4-[4-(dimethylaminomethyl)benzyl]piperidine;

(f) N-(benzylthio)thiocarbonyl-4-[4-(dimethylaminomethyl)benzylidene]piperidine;

(g) N-(4-chlorophenoxy)thiocarbonyl-4-[4-(dimethylaminomethyl)-benzyl]piperidine;

(h) N-(4-chlorophenoxy)carbonyl-4-[4-(dimethylaminomethyl)-benzyl]piperidine;, (i) N-benzyloxycarbonyl-4-[4-(dimethylaminomethyl)benzyl]piperidine;

(j) 4-[4-(dimethylaminomethyl)benzyl]-N-(4-methylphenoxy)carbonylpiperidine;

(k) 4-[4-(dimethylaminomethyl)benzyl]-N-(4-methylphenoxy)thiocarbonylpiperidine; and (l) 4-[4-(dimethylaminomethyl)benzyl]-N-(4-fluorphenoxy) carbonylpiperidine, or a pharmaceutically acceptable salt thereof.

6. Physiologically acceptable salts of the compounds according to one of claims 1 to 5 with inorganic or organic acids.

7. A pharmaceutical composition containing a cholesterol biosynthesis inhibiting amount of compound according to one of claims 1, 2, 3, or 4.

8. A method for the treatment or prophylaxis of hypercholesterolaemia, hyperlipoproteinaemia, hypertriglyceridaemia, and the resulting atherosclerotic vascular changes with their consequent diseases selected from the group consisting of coronary heart disease, cerebral ischaemia, Claudicatio intermittens, and gangrene, which method comprises administering to a host in need of such prophylaxis or treatment a therapeutic amount of a compound in accordance with one of claims 1, 2, 3, or 4.

* * * * *